United States Patent
Hermanson et al.

(10) Patent No.: US 7,884,061 B1
(45) Date of Patent: Feb. 8, 2011

(54) CONCENTRATED LIQUID SOAP FORMULATIONS WITH GREATER THAN 50% LONG CHAIN SOAP AND FATTY ACID HAVING READILY PUMPABLE VISCOSITY

(75) Inventors: Kevin Hermanson, Hamden, CT (US); Florencio V. Ratuiste, Union, NJ (US); Martin Swanson Vethamuthu, Southbury, CT (US); Badreddine Ahtchi-Ali, Newtown, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 12/539,776

(22) Filed: Aug. 12, 2009

(51) Int. Cl.
*A61K 7/50* (2006.01)

(52) U.S. Cl. .................. 510/130; 510/159; 510/424; 510/481; 510/505

(58) Field of Classification Search .................. None
See application file for complete search history.

(56) References Cited

U.S. PATENT DOCUMENTS

| | | | |
|---|---|---|---|
| 1,971,375 | A | 8/1934 | Hoyt |
| 3,723,328 | A | 3/1973 | Pelizza |
| 4,310,433 | A | 1/1982 | Stiros |
| 4,387,040 | A | 6/1983 | Straw |
| 5,147,574 | A | 9/1992 | MacGilp et al. |
| 5,149,574 | A | 9/1992 | Gross et al. |
| 5,158,699 | A | 10/1992 | MacGilp et al. |
| 5,296,157 | A | 3/1994 | MacGilp et al. |
| 5,296,158 | A | 3/1994 | MacGilp et al. |
| 5,308,526 | A | 5/1994 | Dias et al. |
| 5,952,286 | A | 9/1999 | Puvvada et al. |
| 6,077,816 | A | 6/2000 | Puvvada et al. |
| 7,351,749 | B2 | 4/2008 | Divone et al. |

FOREIGN PATENT DOCUMENTS

| | | |
|---|---|---|
| DE | 560 980 | 10/1932 |
| DE | 598 569 | 6/1934 |
| DE | 1 955 557 | 11/1969 |
| DE | 10 2005 008 837 | 8/2006 |
| GB | 512 642 | 9/1939 |
| GB | 601 651 | 5/1948 |
| GB | 699 189 | 11/1953 |
| GB | 842 813 | 7/1960 |
| GB | 887 247 | 1/1962 |
| GB | 1 235 292 | 6/1971 |
| GB | 1 427 341 | 3/1976 |
| GB | 2 005 297 | 4/1979 |
| GB | 2 090 277 | 7/1982 |
| JP | 60 130 699 | 7/1985 |
| JP | 2000/273495 | 10/2000 |
| JP | 2002/226359 | 8/2002 |
| JP | 2004/210833 | 7/2004 |
| JP | 2006/206525 | 10/2006 |
| JP | 2006/282591 | 10/2006 |
| WO | 95/13355 | 5/1995 |
| WO | 97-05857 | 2/1997 |
| WO | 97/27279 | 7/1997 |
| WO | 04/054695 A1 | 7/2004 |
| WO | 2004/080431 | 9/2004 |
| WO | 2005/018760 | 3/2005 |

OTHER PUBLICATIONS

Pursuant to MPEP § 2001.6(b) applicants bring the following co-pending application to the Examiner's attention: Applicant: Harmanson, et al., Filed: Aug. 12, 2009, Concentrated Liquid Soap Formations Having Readily Pumpable Viscosity.

*Primary Examiner*—Necholus Ogden, Jr.
(74) *Attorney, Agent, or Firm*—Ronald A. Koatz

(57) ABSTRACT

The present invention provided concentrated soap compositions, particularly those where long chain ($>C_{14}$) soap and fatty acid comprise >50% of soap and fatty acid. The compositions are formulated in such reasons that, quite unpredictably, despite high soap concentration, they have viscosity which allow them to be pumped from, for example, consumer packaging (e.g., bottles) and/or transit or storage points during manufacture (e.g., pipes, storage tanks, etc.).

12 Claims, No Drawings

CONCENTRATED LIQUID SOAP FORMULATIONS WITH GREATER THAN 50% LONG CHAIN SOAP AND FATTY ACID HAVING READILY PUMPABLE VISCOSITY

FIELD OF THE INVENTION

The present invention relates to soap formulations, particularly liquid soap formulations, with high concentration of soap, and wherein greater than 50% of soap and fatty acid are long chain ($>C_{14}$). Using formulation and processing criticalities, applicants have found a way in which these high concentration soaps can be readily dispensed (have correct rheology) from, for example, tube, bottle, pump or such dispensers.

BACKGROUND OF THE INVENTION

The rapid growth in human population and the changing economic environment are placing ever increasing demand on world water supplies. Because of water scarcity over much of the world, for example, it is important to prepare liquid cleansing products with as little water as possible. Low water cleansing products offer an environmentally friendly cleansing route which lowers strain on water supply. In the current invention, applicants have provided precisely such low water (high soap) cleansers, which are formed by replacing water with a dense liquid crystalline surfactant phase. Quite unpredictably, these formulations are formulated in a manner that, despite being concentrated products, they can be readily dispensed by hand by the end user consumer.

High concentration soap formulations (i.e., formulations in which fatty acid soap comprises >50%, preferably >50 to 80%, more preferably 55 to 80% by wt. and, more preferably, 60-80% by wt. of the formulation) typically have a solid or thick gel-like rheology at room temperature. Because of this rheology, such formulations are difficult to pump while in production and are extremely difficult to use as personal cleansers dispensed from a tube, bottle, pump or tottle.

While not wishing to be bound by theory, it is believed that the thick rheology associated with high concentration liquid soap composition is the result of the large amount of hexagonal and solid surfactant phases present in the soap at high concentration.

Unpredictably, applicants have found that if the ratio of free fatty acid to soap (e.g., percent of neutralized soap) in these concentrated soap/free fatty acid liquid soap formulations (e.g., percent of soap neutralized) is maintained within defined critical ranges; and, further, that if (1) concentrations or percentage of soap with specifically defined preferred counterion; (2) preferred percentage of saturation versus unsaturation of fatty acid soap and free fatty acid chain lengths; (3) chain length distribution of fatty acid soap and free fatty acid; (4) amount synthetic surfactant (if any); and (5) concentration of solvent (e.g., water, alkylene, glycol) are all selected and maintained within critically defined parameters, then the amount or degree of hexagonal and solid surfactant phase formation can be controlled such that a highly concentrated liquid soap can be made which has a pumpable viscosity (as specifically defined below). If these parameters are not carefully maintained, on the other hand, the viscosities quickly rise and formulations become difficult or impossible to pump (again, outside of ranges defined by the invention).

It should be noted that when we speak of "pumpable" or "flowable" viscosity, this is a rheological property which can be critical at many different stages in the manufacturing or distribution process. Thus, it can be critical to keep pumpable viscosity for example in the mixing stage of a manufacturing tank; in filing and/or discharging fluid to manufacturing or storage tanks; and/or in filling product into final packaging.

One great benefit of this invention is that the liquids made by this specific selected blend of neutralized soap and unneutralized fatty acids can be made in what would normally be used as a bar production facility. Unexpectedly, and unpredictably, applicants have found that the blends of fatty acid and soap used in the bar production process can be used to produce concentrated liquids as well (i.e., assuming the criticalities noted above are maintained).

In addition, concentrated liquids having the correct rheology and which are produced by the process of the invention can be sold as a "concentrated liquid product" whereby the consumer can be instructed to dilute the product at home (resulting in both environmentally friendly packaging and tremendous cost savings); or the concentrated liquid can be transported to a different place and later diluted as part of the production process. In the latter case, this allows the producer to produce more cheaply than when normally making liquid soap/syndet composition (e.g., reduction in transportation costs due to use of concentrates rather than transporting heavy water-containing product). As indicated above, tremendous efficiencies between bars and liquids are also found because any excess capacity from bar manufacturing sites may be used to make liquids.

The key, as noted above, is to obtain a final concentrated liquid formulation in which variables such as (1) ratio of neutralized soap to unneutralized fatty acid; (2) counterion; (3) chain length of fatty acid soaps and free fatty acids; (4) synthetic surfactant, if any; (5) and solvent are critically controlled to obtain viscosities below a defined level and defined by a dispensing force needed to dispense the product. This goal in turn may be achieved either by controlled neutralization of fatty acid; or by using mixtures of free fatty acid and fully neutralized soap such that resulting formulation falls within defined formulation parameters where this defined pumpable or squeezable rheology is obtained.

It should be noted that there is interplay between variables and these variables can be adjusted as long as the overall goal of maintaining a low dispensing force is maintained. Thus, for example, the degree of neutralization or exact percent of long chain or low chain length soap/fatty acids may be closer to the upper or lower ranges in which case adjustments can be made to solvent level or level or synthetic surfactant.

In one embodiment of the invention, for example, there may be present only soap/fatty acid and neutralizing solvent such as potassium hydroxide (e.g., no viscosity reducing co-solvent such as dipropylene glycol, propylene glycol). Such embodiment would minimize the level of long chain length, fatty acid/soaps (which tend to increase viscosity) and certainly ensure their level is within defined ranges. This first embodiment is specifically claimed in a co-pending application filed on same date as the subject application. In another embodiment of the invention, the concentrate could tolerate higher levels of longer chain length soaps/fatty acids but would also have some required level of synthetic surfactant and/or viscosity reducing co-solvent to ensure the dispensing force is within defined parameters. This second embodiment is clamed by the subject application.

As far as applicants are aware, the art does not disclose the specific parameters required to obtain concentrated soap liquids of the invention, or a method of obtaining these liquids such that the liquid soap has a pumpable, readily pourable rheology, i.e., measured by dispensing force which is defined in the protocol. Specifically there is nothing in the art which would teach or suggest the person of ordinary skill either that this is a problem or how to begin to solve such problem.

GB 699 189 is an example of references disclosing compositions made by neutralization of fatty acids with caustic potash. Although the fatty acids of the resulting liquid cleansers are neutralized, there is no indication of partial neutralization, or of the resulting critical, specific ratios, of fatty acid to soap. Further, there is no disclosure that such specific ratios, or of any of the other criticalities of saturation, chain length, etc. which are required to obtain the pumpable (e.g., squeezable), concentrated soap liquids of the invention having defined viscosity. This reference is typical of many older references from before 1960.

More recent references include those which use soap at much lower levels. Examples of such references include WO 95/13355, WO 05/18760 and WO 97/27279.

U.S. Pat. Nos. 5,952,286 and 6,077,816, both to Puvvada, relate to the use of free fatty acid to form lamellar structures in liquid cleansing products having 9 to 50% surfactant concentration. Overall concentrations of surfactant in these references are lower than the overall concentration of surfactant (e.g., soap plus fatty acid) of the compositions of the invention and the concentrations of water are higher than those of our invention. Further, there is no recognition of use of specific ratios of fatty acid to soap or of other criticalities noted.

U.S. Pat. No. 7,351,749 to Divone et al. relates to the process for manufacture of personal care products using concentrated water phase. The reference is not related to concentrated soaps or to specific ratios of fatty acid to the soap.

U.S. Pat. Nos. 5,296,158 and 5,149,574 to MacGilp disclose compositions with potassium soap and free fatty acid. Concentrations of water are 55-90% compared to top solvent concentration (water/solvent) of 40% in our invention. U.S. Pat. No. 4,310,433 to Stiros discloses mixtures of neutralized and unneutralized fatty acids where fatty acids are mixtures of saturated and unsaturated. The compositions again comprise 50-95% water, levels of solvent well above those of our invention. Various other references to MacGilp, (U.S. Pat. No. 5,158,699; U.S. Pat. No. 5,296,157) also have much higher levels of water/overall solvent.

U.S. Pat. No. 5,308,526 to Dias discloses composition with $K^+$ soap and free fatty acids. They comprise 35-70% water. The compositions have much less than 50% soap.

WO 2004/080431 to Unilever relates to method of preparing personal care compositions from concentrate. There appears to be no recognition of a concentrate having critically specific levels of neutralization (ratio of fatty acid to soap) or other noted variables which provide a rheology allowing concentrated soap formulations to be pumped or readily dispensed. The reference also fails to disclose a separate concentrated liquid (e.g., as separate stand alone product) which can be sold to consumers for possible dilution at home.

GB 2005297 (Unilever) discloses liquid soap compositions comprising potassium soap, 0-20% glycerol, 5-20% alkylene glycol, 0-10% free fatty acids and 20-50% water. Levels of soap are well below the 50% level of the subject invention.

GB1427341 (Unilever) discloses potassium soap crystals in aqueous glycerin solution comprising 12-40% glycerol and 20-50% $H_2O$. Again, levels of soap are well below those of compositions of the invention.

JP 2006/282,591 and JP 2002/226,359 relate to face wash creams. Neither appears to disclose criticality of fatty acid to soap in combination with other criticalities to yield a high concentrated, pumpable liquid soap.

None of the reference discloses high soap (>50% by wt.) compositions having a critical ratio of fatty acid to soap or combination with criticalities of saturation, chain length, solvent etc. to produce pumpable, concentrated liquid soaps. There also is no reference relating to sale of such specific compositions as stand alone concentrates with instructions for home dilution.

BRIEF DESCRIPTION OF THE INVENTION

Unexpectedly, and quite unpredictably, applicants have now found that, if the ratio of unneutralized fatty acid to neutralized fatty acid soap (in a concentrate solution where soap comprises >50%, preferably 60% of concentrate) is kept within a specific critical window, in combination with other critical parameters noted below, the resulting concentrate will have a rheology that allows it to be pumped and/or dispensed. Such pumpability is defined as a formulation which can be dispensed by a force of less than 300N at steady state when measured at temperatures of 23° C. Measurement can also be made at 12° C. although, for purposes of measurement definition, the temperature is preferably 23° C. Measurement details are defined in more detail in the protocol below. It should be noted that, although it is probably not possible for humans, unassisted by technology, to generate a force of 300N, tubes of varying orifice size can be designed which allow for dispensing of fluid at values closer to the upper ranges of Newton force required by the protocol.

In one embodiment, the invention relates to a concentrated soap formulation, which, optionally, can be moved (as an intermediate for preparation of final product at same or other site); or which is sold as a "final" product (e.g., to be diluted by consumer elsewhere). In a second embodiment, the invention relates to a packaged product containing said concentrated solution. Finally, in a third embodiment, the invention relates to a process for preparing concentrated liquids which process comprises either (a) neutralizing soap stock comprising oils, triglycerides and fatty acids to provide soap and obtain required parameters (e.g., ratio of fatty acid to neutralized soap); or (b) mixing already neutralized soap and free fatty acid to form mixture having desired criteria.

In one compositional embodiment of the invention (subject of co-pending application filed same date), the present application comprises concentrated soap formulation and does not necessarily comprise synthetic and/or co-solvent (other than water and/or neutralizing hydroxide solution). This embodiment comprises:

(a) >50% by wt. fatty acid soap, preferably >50 to 80%, more preferably 55 to 80%, even more preferably 60 to 80% fatty acid soap;

(b) free fatty acid at concentration such that soap to free fatty acid ratio is about 2:1 to 20:1 on a weight basis, preferably 2.5:1 to 12:1. Typically this reflects a neutralization (if soap is formed in-situ versus combining fatty acid and already pre-formed soap) of about 60 to about 90% neutralization;

(c) 0% to 30% by wt., preferably 1% to 20% by wt, more preferably 1% to 15% by wt. (even more preferably 10% by wt. or below) of synthetic non-soap surfactant (e.g., used to help reduce viscosity to defined "pumpable" goal), wherein said synthetic, if used, comprises at least one anionic surfactant and, more preferably, comprises a combination of anionic and amphoteric surfactant wherein anionic comprise more than half of such mixture; although synthetic, if present, helps serve as a viscosity modifier, if short chain soap and fatty acid definitely comprise ≧50% of total, then the synthetic and/or co-solvent (other than water) are not absolutely required; and (d) 10-40% by wt. solvent wherein solvent includes combination of water and/or co-solvents preferably selected from alkylene glycols (e.g., propylene glycol, dipropylene glycol, mixtures, etc.); as noted, where short chain soap and fatty acid comprise ≧50%, then co-solvent (other than water) is not required so, preferably, the 10-40% solvent comprises only water, wherein the soap counterion is preferably potassium and/or amine based counterion (e.g., sodium counterions can be used, but tend to increase viscosity);

wherein soap and fatty acid chains may be a mix of saturated and unsaturated, but are preferably >75%, more preferably 80% to 100%, even more preferably 96% to 100% and even more preferably 100% saturated;

wherein soap and fatty acid comprise a mixture of long ($>C_{14}$-$C_{30}$) and short ($\leq C_{14}$) chain and preferably comprise ≧50%; more preferably >60, even more preferably >75% short chain (as indicated above, where short chain is definitely ≧50%, synthetic and/or co-solvents are not required although of course small amounts, e.g., less than 5% by wt., preferably less than 3%, more preferably less than 1% of one or both may be used);

and wherein the "pumpable" viscosity achieved by maintaining ratio of soap to fatty acid (e.g., through neutralization) and maintaining other noted variable within defined parameters is defined as a dispensing force of less than 300 Newtons (N) measured at steady state and at temperature of 23° C. or 12° C. as defined in the protocol.

In a second compositional embodiment of the invention (subject of the present application), the invention comprises concentrated soap formulation where short chain fatty acid and soap ($\leq C_{14}$) is less than 50% total fatty acids and soap. Long chain ($>C_{14}$) may comprise >50% to 80%, or possibly even more. In this embodiment, viscosity modifier such as some synthetic and/or co-solvent is required to ensure pumpable viscosity as defined in the protocol.

More specifically, this embodiment comprises:
(a) >50% by wt., preferably >50% to 80%, more preferably 55% to 80% and even more preferably 60 to 80% fatty acid soap;
(b) free fatty acid in the same ratio as defined for the first compositional embodiment;
(c) 0% to 30%, preferably 1% to 20%, more preferably 1% to 15%, even more preferably 5% to 15% synthetic, preferably comprising at least one anionic; and
(d) 10% to 40% solvent which preferably will comprise 1% to 15% solvent other than water;

wherein at least 1% to 10%, preferably at least 2 to 10% by wt. of total (c) and/or solvent other than water in (d) must be present and where such other solvent is preferably an alkylene glycol;

wherein counterion and level of saturation are as defined for first compositional embodiment;

wherein long chain soap ($>C_{14}$) comprises >50% to 80% of fatty acid/soap chain length; and wherein pumpable viscosity combined is defined as a dispensing force of less than 300 Newton (N) at steady state as defined in protocol.

In another embodiment, the invention provides a packaged personal care/personal wash product which comprises:
(a) a container or bottle comprising a label or advertising intended for sale or distribution to consumers; and
(b) concentrated soap formulation as defined in the compositional embodiments of the invention.

In this embodiment, the container or a package in which the container is held may contain instructions to the consumer as to how and when to dilute the concentrated product for ultimate use.

In yet another embodiment, the invention comprises a process for preparing a concentrated soap liquid according to either compositional embodiment which process comprises:
(a) reacting a soap stock comprising oils, triglycerides, fatty acids and mixtures thereof with a neutralizing solution, preferably a caustic solution such as KOH, to obtain composition where ratio of soap to free fatty acid is between 2:1 to 20:1, preferably 2.5:1 to 12:1 on weight basis (generally corresponding to level of 60-90% neutralization), and subsequently or simultaneously combining soap stock and neutralizing solution with 0% to 30% synthetic surfactant, and 10 to 40% solvent; or
(b) mixing already neutralized soap and free fatty acid to form mixture having ratios and/or neutralization levels noted above and subsequently combining with same levels of synthetic surfactant, and solvent also noted.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental example, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y" it is understood that all ranges combining the different endpoints are also contemplated. Further in specifying the range of concentration, it is noted that any particular upper concentration can be associated with any particular lower concentration. Where the term "comprising" is used in the specification or claims, it is not intended to exclude any terms, steps or features not specifically recited. For the avoidance of doubt, the word "comprising" is intended to mean "including" but not necessarily "consisting of" or "composed of". In other words, the listed steps, options, or alternatives need not be exhaustive. All temperatures are in degrees Celsius (° C.) unless specific otherwise. All measurements are in SI units unless specified otherwise. All documents cited are—in relevant part—incorporated herein by reference.

DETAILED DESCRIPTION OF THE INVENTION

The present invention relates to liquid soap formulations with highly concentrated amounts of soap, yet which maintain a viscosity/rheology suitable for these concentrated soaps to be pumped from a reservoir, container or bottle, as defined by formulations which can be dispensed by a dispensing force less than 300N at steady state measured at 23° C. defined using protocol below. Unexpectedly, applicants have found that, only when the ratio of neutralized soap to unneutralized free fatty acid is maintained within strict, critically defined limits, and parameters such as counterion, saturation, chain length of fatty acids and soap; solvent and/or synthetic surfactant levels etc. are controlled, only then is it possible to obtain such concentrated soap formulations (i.e., >50% soap)

which maintain the characteristics of a suitable pumpable liquid (defined by a dispensing force as noted).

In a compositional embodiment, the invention is directed to the concentrated liquid formulations themselves. Those compositions are defined by ratios of neutralized soap to fatty acid (which also correspond to levels of neutralization), where the critical rheology is obtained. The formulations can be obtained by controlled neutralization and/or by mixing fatty acids and soap to fall within the critically defined parameters. One aspect of the compositional invention is directed to compositions where preferred $\geq 50\%$ of soap/fatty acid have chain length$\leq C_{14}$ and wherein use of synthetic surfactant and/or certain co-solvents is not required, and a second aspect is directed to composition having >50% chain length>$C_{14}$ and where minimum level of synthetic and/or co-solvent (solvent other than water, e.g., alkylene glycol) is required. Although it is theoretically possible component (d) could be only co-solvent other than water, as a practical matter the co-solvent preferably comprises 1% to 50% of all solvent (e.g. 50% to 99% is water).

In a second embodiment, the invention is defined by a packaged consumer product which comprises the packaged bottle or container comprising the concentrated formulation of the first compositional embodiment. Preferably, the label provides instructions to consumers on how to add water to effectively use the concentrates.

In a third embodiment, the invention comprises a process for preparing these unique concentrated soap liquids which process essentially comprises controlling the neutralization process and/or reactants to ensure the final product has the criticality defined ratios which will ensure the unpredictable pumpable rheology.

The invention is described in greater detail below.

The composition of the invention comprises as noted, >50% by wt. fatty acid soap, preferably >50% to 80% by wt., more preferably 55% to 80%, even more preferably 60 to 80% fatty acid soap.

In addition, compositions of the invention comprise free fatty acid and indeed, it is the ratio of free fatty acid to soap which helps define (along with other variables discussed below) the rheology which is required for "pumpability".

More specifically, the concentration of free fatty acid to soap (obtained either by controlled neutralization or by simple mixing) is such that ratio of soap to free fatty acid is about 2:1 to 20:1, preferably 2.5:1 to 12:1. This latter ratio typically reflects a neutralization (if formed in-situ) of about 60 to 90% neutralization.

Further the counterion on soap; the degree of saturation or unsaturation; chain length distribution in soap and/or fatty acid, and levels of synthetic and/or solvent can be critical in determining final rheology (e.g., what dispensing force is required for pumping or dispensing). As indicated, depending in particular on chain length distribution, the levels of synthetic and/or solvent can also be critical in obtaining the right feeling.

Although any salt counterion can be used, preferably the counterion for the soap is potassium. Sodium counterions tend to increase the viscosity and may raise the viscosity above that required by the invention depending on interplay of other factors (for example, use of sodium might require also greater use of synthetic and/or co-solvent). Amine based counterions (trialkanolamine, ammonium, etc.) may have similar effect as potassium and can also be used. Other counterions which may be used include calcium, magnesium and zinc. As indicated, preferably the goal is to use counterions which have the least effect on viscosity and which will allow, together with other factors, pumpability as defined to be maintained.

In particular, it is preferred to use counterions which are 50% to 100%, more preferably 80% to 100% and even 100% potassium and/or amine (e.g., trialkanolamine). More preferably, counterion can be >75%, preferably 80% to 100% potassium.

It is also preferred to use saturated fatty acid and soap chains. Saturated chains generally have fewer color (e.g., browning) or odor problems and have generally good lather. Some unsaturates may be used, however, in that they help keep the product softer or pastier, for example. Typically, it is preferred to use >75%, more preferably 80% to 100%, even more preferably 96% to 100% and even 100% saturated chains.

Fatty acids and soaps of chain length $C_{14}$ or less are also generally preferred. Typically, a product of chain length only above $C_{14}$ would have very thick rheology. As discussed above, however, although having >50% short chain length ($\leq C_{14}$) is preferred (and is encompassed by first compositional embodiment of the invention), a composition comprising <50% $C_{14}$ chain length, i.e., having >50% to 80%>$C_{14}$ chain length may be used but, in such cases (as in the second compositional embodiment), a minimum amount of synthetic surfactant and/or co-solvent (other than water) are used. Preferably, if solvent is used, it is an alkylene glycol solvent, such as, for example, dipropylene glycol or propylene glycol. As also noted above, use of synthetic and/or co-solvent as viscosity modifiers may also be found if sodium (or other counterion that ensures viscosity too much) is used as soap counterion. As indicated previously, while theoretically possible that all solvent is solvent other than water, this is very difficult to achieve and generally solvent other than water comprises from 1% to 50% of solvent, e.g., water comprises 50% to 99%. The key is to manipulate ratios, counterions, synthetic and/or solvent to ensure the dispensing force of the resulting solution as per test described in the protocol is less than 300 Newtons (N) at steady state when measured at defined temperature.

Compositions of the invention should also comprise 0% to 30%, preferably 1% to 20%, more preferably 1% to 15%, even more preferably 1% to 10% by wt. synthetic non-soap surfactant. Again, in formulation with >50% chain length of $C_{14}$, no synthetic may be needed whereas, if >50% is >$C_{14}$, some synthetic and/or co-solvent is required.

While syndet (synthetic detergent) is not required to produce, for example, a soft paste at 23° C., the syndet can be used to reduce low temperature viscosity (as can co-solvent, as noted below), for reasons noted.

Typically, synthetic surfactant, if present, will comprise at least one anionic surfactant (e.g., alkyl sulfate or isethionate). Preferably, the compositions will comprise a combination of anionic synthetic and amphoteric surfactant (e.g., betaine), especially when anionic comprises 50% or greater of such mixture of synthetics.

The concentrate compositions of the invention further comprise 10% to 40% by wt. solvent. The solvent comprises water or caustic neutralizing solution and may further comprise non-water co-solvent, e.g., polypropylene glycol.

Generally, the greater the amount of co-solvent, the less water required. It is also easy to keep viscosity within required range as more co-solvent and less water is used.

Viscosity reducing co-solvents of the invention include propylene glycol, dipropylene glycol, polypropylene glycol, and many other such related solvents as would be well known to those skilled in the art.

In one embodiment, glycerin can be used as co-solvent. While glycerin does not enhance low temperature stability, low viscosity product can be made with small amounts of glycerin. At levels above about 10%, higher amounts of co-solvent and/or synthetic surfactant might have to be used.

Finally, a suitable pumping viscosity is defined as a product which requires a dispensing force of less than 300N, measured as defined in protocol.

The concentrate formulations of the invention, in addition to comprising soap/fatty acid, solvent and synthetic surfactant, may also comprise various benefit agents and/or other ingredients which can typically be used in flowable, liquid personal care formulations.

Benefit agent may be any material that has potential to provide an effect on, for example, the skin.

The benefit agent may be water insoluble material that can protect, moisturize or condition the skin upon deposition from compositions of invention. These may include silicon oils and gums, fats and oils, waxes, hydrocarbons (e.g., petrolatum), higher fatty acids and esters, vitamins, sunscreens. They may include any of the agents, for example, mentioned at column 8, line 31 to column 9, line 13 of U.S. Pat. No. 5,759,969, hereby incorporated by reference into the subject application.

The benefit agent may also be a water soluble material such as glycerin, polyols (e.g., saccharides), enzyme and $\alpha$- or $\beta$-hydroxy acid either alone or entrapped in an oily benefit agent.

The compositions may also comprise perfumes, sequestering agents such as EDTA or EHDP in amounts 0.01 to 1%, preferably 0.01 to 0.05%; coloring agents, opacifiers and pearlizers such as zinc stearate, magnesium stearate, $TiO_2$, mica, EGMS (ethylene glycol monostearate) or styrene/acrylate copolymers.

The compositions may further comprise antimicrobials such as 2-hydroxy 4,2'4'trichlorodiphenylether (DP300), 3,4, 4"-trichlorocarbanilide, essential oils and preservatives such as dimethyl hydantoin (Glydant XL 1000), parabens, sorbic acid, etc.

The compositions may also comprise coconut acyl mono or diethanol amides as suds boosters, and strongly ionizing salts such as sodium chloride and sodium sulfate may also be used to advantage.

Antioxidants such as, for example, butylated hydroxyl toluene (BHT) may be used advantageously in amounts of about 0.01% or higher if appropriate.

Cationic conditioner which may be used including Quatrisoft LM-200 Polyquaternium-24, Merquat Plus 3330- Polyquaternium 39; and Jaguar®type conditioners.

Composition may also include clays such as Bentonite® claims as well as particulates such as abrasives, glitter, and shimmer.

In a second embodiment of the invention, the invention relates to a packaged personal care or personal wash product which comprises a container or bottle which container or bottle comprises a label (e.g., indicating product logo or insignia) and/or advertising (e.g., print copy or other form of advertising) and which is intended for sale or distribution. The product comprises the soap formulation as set forth in the compositional embodiment of the invention.

In a preferred embodiment, the package or container has instructions which directs the consumer how and when to dilute the concentrated soap for use at home or elsewhere.

This packaged product can be used, for example, to save on cost of transporting a much heavier product to the point of sale (e.g., market) by the producer of the product and further to save cost (weight/energy, etc.) of the consumer to transport to their point of use. Further, it provides an ecologically friendly product which can be used as a source of advertising and good will.

In a third embodiment, the invention relates to a process for making concentrated soap.

This can be done either by reacting soap stock and fatty acid to neutralize and obtain ratios as required by the invention (e.g., in situ) that meet required viscosity targets for obtaining "pumpability"; and/or by mixing already prepared soap and fatty acid to obtain same desired ratios. In either case, the fatty acid and soap (preferred or not) are further reacted with optional synthetic and with solvent to form final concentrates.

EXAMPLES

Protocol

Rheological Measurement Protocol

In the rheological measurement used to determine pumpablility, a tube which is 31.4 mm in diameter is used. This tube is open on one end and sealed at the other end with an orifice plate which has a hole that is 3 mm in diameter and 12 mm in length. 150 ml of product is first loaded into the tube through the open end. A piston is then inserted into the open end of the tube and the product is pushed through the orifice at a flow rate of 0.5 ml/sec using an Instron universal testing machine. Using the Instron the force required to achieve this flow rate at steady state is measured. To account for frictional forces, a second run is then conducted without any product in the tube at the same piston velocity. The force required to push the piston without product is then subtracted from the force required to push the product through the orifice. This measured force is defined as the product dispensing force. According to the subject invention, products which are defined as "pumpable" require a force of less than 300 N at steady state. Steady state is defined as the longest measured interval over which the measured dispensing force is approximately consistent. In order for the measurement interval to be considered the steady state interval, more than 0.75 ml of product must be dispensed during the interval. This rheological measurement simulates flow from a tube and is a direct determination of the amount of force required to dispense the product from a tube. The measurements were conducted at two temperatures, 23° C. and 12° C. although, for purposes of keeping definition constant, the measuring temperature is preferably 23° C. The temperature was held constant using a temperature controlled jacket surrounding the tube.

In short, pumpability is defined as requiring less than 300N of force to extrude through an orifice which is 3 mm in diameter and 12 mm in length as described above. Primarily, this test is to be conducted at temperature of 23° C. (e.g., about room temperature).

Sample Preparation

The examples were made by first heating the fatty acid blend in a mixer to a temperature between 65-80° C. Of the total caustic required 75%-90% was added to the melted fatty acids while mixing at low speed during a period of $\geq$15 minutes. The mixing speed used was sufficient to thoroughly react the caustic. Synthetic detergent (SLES, CAPB or sodium lauryl sarcosinate) and co-solvent (dipropylene glycol, i.e., DPG or PPG-9) were then mixed into the fatty acid soap blend. After the addition of synthetic detergent and co-solvents, the remaining caustic was added and the mixed well. The final product was then cooled to room temperature.

DEFINITIONS

| | |
|---|---|
| SLES = | sodium lauryl ether sulfate |
| CAPB = | cocoamidopropyl betaine |
| PPG = | polypropylene glycol |
| HT = | hard topped |

EXAMPLES

Using the rheological protocol noted above, a commercial soap bar was tested. The soap bar represents the low water soap formulations which are in the prior art. These formulations have a high viscosity and can not be dispensed from a tube. The force which would be required for dispensing a soap bar according to the applied rheological protocol is 5160 N. This force is well above the critical range of the subject invention of 0-300 N.

For the raw materials used in the example formulations the chain length distributions are given in the table below:

| Chain Length | HT Coconut Fatty Acid | Lauric Acid | Myristic Acid | Palmitic Acid | Commercial Stearic Acid |
|---|---|---|---|---|---|
| Short Chain (<C8) (wt %) | 0 | 0 | 0 | 0 | 0 |
| Capric C10 (+C8) (wt %) | 0 | 0 | 0 | 0 | 0 |
| Lauric C12 (+C11) (wt %) | 55.1 | 100 | 0 | 0 | 0 |
| Myristic C14 (+C13) (wt %) | 21.9 | 0 | 100 | 2 | 2 |
| Palmitic C16 (+C15) (wt %) | 11.4 | 0 | 0 | 92 | 45 |
| Stearic C18 (+C17) (wt %) | 11.4 | 0 | 0 | 6 | 52 |
| Long Saturates >= C19 (wt %) | 0.2 | 0 | 0 | 0 | 0 |
| Other | 0 | 0 | 0 | 0 | 1 |

Examples 1-3 and Comparatives A & B

For a mixture of short chain potassium soaps, a critical window of neutrality exists where the soap mixture has a low enough viscosity (as defined in protocol) for dispensing from a tube. The examples below (Example 1-3 and Comparatives A & B) show that for neutralizations where the final soap: fatty acid ratio is between 2:1 and 20:1, a low viscosity soap mixture is obtained at room temperature. In all of the examples, more than 75% of the fatty acid chains used have chain length less than or equal to $C_{14}$.

| Examples 1-3 and Comparatives A & B | | | | | |
|---|---|---|---|---|---|
| Ingredients by wt % Formulation Number | Comp A | 1 | 2 | 3 | Comp B |
| HT Coco Fatty Acid | 53.6% | 51.4% | 0.0% | 47.6% | 45.9% |
| Lauric Fatty Acid | 0.0% | 0.0% | 34.1% | 0.0% | 0.0% |
| Myristic Fatty Acid | 21.4% | 20.5% | 34.1% | 19.0% | 18.3% |
| KOH (45 wt %) | 25.0% | 28.1% | 31.8% | 33.4% | 35.8% |
| Soap:Fatty Acid | 1.75 | 2.74 | 4.71 | 10.50 | Infinite |
| Solvent Concentration | 17% | 19% | 22% | 23% | 25% |
| Dispensing Force @ 23° C. | 412 | 232 | 53 | 38 | 1061 |
| Dispensing Force @ 12° C. | | | | 1106 | |
| % of Fatty acid and soap with chain length >$C_{14}$ | 16.4% | 16.4% | 0.0% | 16.4% | 16.4% |
| % of neutralization of final composition | 60% | 70% | 80% | 90% | 100% |

As seen from examples above, when soap to fatty acid ratio was in ranges of invention and percent of fatty acid and soap having chain length≦$C_{14}$ is greater than or equal to 50% (Example 1-2), the dispensing force was clearly less than 300N (defining pumpable viscosity). When outside such ratios (Comparative A has ratio of 1.75 and comparative B has infinite ratio), dispensing force is well above 300N. It is noted that these compositions comprise no solvent other than water and no syndet and that, measured at 12° C., viscosity is not pumpable as defined.

Example 4 and Comparative C

If more than 50% of the used fatty acid has a chain length greater than $C_{14}$, the soap mixture is too thick to be dispensed from a tube, even when measured at 23° C. (Comparative C). However, with the addition of co-solvent and synthetic surfactant (e.g., SLES and CAPB), the viscosity is within a range which is suitable for tube dispensing (Example 4).

| Ingredients by wt % Formulation Number | Comp C | 4 |
|---|---|---|
| HT Coco Fatty Acid | 29.5% | 0.0% |
| Lauric Fatty Acid | 0.0% | 13.0% |
| Myristic Fatty Acid | 9.5% | 12.2% |
| Palmitic Fatty Acid | 7.5% | 4.5% |
| Stearic Fatty Acid | 22.1% | 23.6% |
| KOH (45 wt %) | 31.5% | 0.0% |
| KOH (85 wt %) | 0.0% | 13.1% |
| SLES (70 wt %) | 0.0% | 9.6% |
| CAPB (28 wt %) | 0.0% | 8.6% |
| DPG | 0.0% | 9.0% |
| Water | 0.0% | 6.4% |
| Soap:Fatty Acid | 9.74 | 10.58 |
| Dispensing Force @ 23° C. | 383 | 38.8 |
| % of Fatty acid and soap with chain length >$C_{14}$ | 51.83% | 51.30% |
| % of neutralization of final composition | 89.38% | 90.14% |
| Solvent in final composition | 21.88% | 30.00% |

As seen, therefore, even though both examples have >50% of chain length greater than $C_{14}$ (which make viscosity higher), the interplay of solvent and synthetic surfactant brings the defined dispensing force from well above 300 (383N) to well below (38.8N).

Examples 5 and 6 and Comparative D

The viscosity of soap formulations are low enough for dispensing from a tube at solvent concentrations between 10 and 40%. Comparative D has a solvent concentration below 10% and is not dispensable from a tube. Examples 3, 5 and 6 have the same fatty acid blend as Comparative Example D but have a solvent concentration in the range of 10 to 40%. All of these formulations have a dispensing force less than 300 N measured at 23° C. Comparative D has less than 10% solvent and much higher dispensing force. Comparison of Examples 3 and 6 also shows that the addition of the co-solvent DPG lowers the dispensing force below 300 N measured at 12° C. (from 1106N to 70N). This demonstrates that co-solvent can be used to improve low temperature dispensability.

| Ingredients by wt %<br>Formulation Number | Comp D | 5 | 6 |
|---|---|---|---|
| HT Coco Fatty Acid | 56.5% | 37.2% | 43.4% |
| Myristic Fatty Acid | 22.5% | 14.8% | 17.3% |
| KOH (45 wt %) | 0.0% | 26.1% | 30.4% |
| KOH (85 wt %) | 21.0% | 0.0% | 0.0% |
| DPG | 0.0% | 0.0% | 8.9% |
| Water | 0.0% | 21.9% | 0.0% |
| Soap:Fatty Acid | 10.49 | 10.50 | 10.50 |
| Solvent Concentration | 8.9% | 40.0% | 30.0% |
| Dispensing Force @ 23° C. | 19094 | 269 | 56.8 |
| Dispensing Force @ 12° C. |  |  | 70 |
| % of Fatty acid and soap with chain length >C14 | 16.45% | 16.45% | 16.45% |
| % neutralization of final composition | 89.97% | 89.98% | 89.98% |

Examples 7-9

Like co-solvents, synthetic surfactant can also be used to reduce or maintain the dispensing force below 300 N, particularly low temperature dispensing. Examples 7-9 are two formulations which demonstrate the effect of synthetic surfactants on partially neutralized soap formulations. When compared to Example 3, the addition of synthetic surfactants reduces the dispensing force at both 23° C. and 12° C.

| Ingredients by wt %<br>Formulation Number | 7 | 8 | 9 |
|---|---|---|---|
| HT Coco Fatty Acid | 37.8% | 37.8% | 37.8% |
| Myristic Fatty Acid | 15.1% | 15.1% | 15.1% |
| KOH (45 wt %) | 26.5% | 0.0% | 0.0% |
| KOH (85 wt %) | 0.0% | 14.0% | 14.0% |
| SLES (70 wt %) | 9.5% | 9.5% | 0.0% |
| CAPB (28 wt %) | 8.5% | 8.5% | 0.0% |
| Sodium Lauryl Sarcosinate (30 wt %) | 0.0% | 0.0% | 30.1% |
| DPG | 0.0% | 3.0% | 3.0% |
| Water | 2.6% | 12.1% | 0.0% |
| Soap:Fatty Acid | 10.50 | 10.49 | 10.49 |
| Solvent Concentration | 30.0% | 30.0% | 30.0% |
| Syndet Concentration | 9.0% | 9.0% | 9.0% |
| Dispensing Force @ 23° C. | 51.5 | 11.2 | 6.7 |
| Dispensing Force @ 12° C. | 460 | 91 | 482 |
| % of Fatty acid and soap with chain length >C14 | 16.45% | 16.45% | 16.45% |
| % of neutralization of final composition | 89.98% | 89.97% | 89.97% |

The invention claimed is:

1. Concentrated soap composition comprising:
   (a) >50% by wt. fatty acid soap;
   (b) free fatty acid at a concentration such that soap to free fatty acid ratio on weight to weight basis is 2:1 to 20:1;
   (c) 0% to 30% by wt. non-soap synthetic surfactant;
   (d) 10% to 40% solvent, where solvent includes combination of water, and co-solvents other than water;
   wherein at least 1% to 10% of total (c) and/or solvent other than water in (d) must be present;
   wherein both soap and fatty acid chain comprise a mixture of saturated and unsaturated chain lengths;
   wherein soap and fatty acid comprise a mixture of long ($>C_{14}$ to $C_{30}$) and short ($\leq C_{14}$) chain length, and long chain length chains comprise >50% of mixture; and
   wherein said concentrated soap has viscosity allowing it to be pumped from a container, wherein said pumpable viscosity is defined by a dispensing force less than 300 N at steady state, measured at 23° C.

2. A composition according to claim 1 wherein ratio of soap to fatty acid is 2.5:1 to 12:1.

3. A composition according to claim 1 wherein 50% to 100% of the soap counterion are potassium counterions.

4. A composition according to claim 1 wherein >75% of soap and/or fatty acids are saturated.

5. A composition according to claim 1 wherein >60% of soap and/or fatty acids are $>C_{14}$.

6. A composition according to claim 1 wherein >50 to 80% of soap and fatty acid chains are $>C_{14}$.

7. A composition according to claim 1 further comprising 1% to 15% synthetic surfactant.

8. A composition according to claim 7 wherein synthetic comprises at least one anionic.

9. A packaged personal care/personal wash product comprising:
   (a) a container or bottle comprising a label or advertising intended for sale or distribution to consumers; and
   (b) concentrated soap composition according to claim 1.

10. A composition according to claim 1 wherein 1 to 50% by wt. of solvent comprises solvent other than water.

11. A composition according to claim 10 wherein other solvent is an alkylene glycol.

12. A process for preparing the concentrated soap composition according to claim 1 which process comprises:
   (a) reacting a soap stock comprising oils, triglycerides, fatty acids and mixtures thereof with a neutralizing solution to obtain composition where ratio of soap to free fatty acid is between 2:1 to 20:1 on weight basis, and subsequently or simultaneously combining soap stock and neutralizing solution with 0% to 30% synthetic surfactant, and 10% to 40% solvent; or
   (b) mixing already neutralized soap and free fatty acid to form mixture having ratio of soap to free fatty acid of 2:1 to 20:1 on a weight basis; and subsequently combining with 0% to 30% by wt. synthetic non-soap detergent and 10-40% by wt. solvent.

\* \* \* \* \*